US005506221A

United States Patent [19]

Andersen et al.

[11] Patent Number: 5,506,221

[45] Date of Patent: Apr. 9, 1996

[54] CONTIGNASTEROL, AND RELATED 3-ALPHA HYDROXY-6-ALPHA HYDROXY-7-BETA HYDROXY-15-KETO-14-BETA STEROIDS USEFUL AS ANTI-INFLAMMATORY AND ANTI-THROMBOSIS AGENTS

[75] Inventors: Raymond J. Andersen, Vancouver; Theresa M. Allen, Edmonton; David L. Burgoyne, Vancouver, all of Canada

[73] Assignees: University of British Columbia, Vancouver; University of Alberta, Edmonton, both of Canada

[21] Appl. No.: 226,179

[22] Filed: Apr. 12, 1994

Related U.S. Application Data

[63] Continuation-in-part of Ser. No. 996,599, Dec. 24, 1992, abandoned.

[51] Int. Cl.[6] .............................. A61K 31/58; C07J 9/00

[52] U.S. Cl. .......................... 514/172; 514/178; 552/553; 540/114

[58] Field of Search ............................ 540/114; 552/553; 514/172, 178

[56] References Cited

U.S. PATENT DOCUMENTS 5,079,239 1/1992 Sun et al. .

OTHER PUBLICATIONS

"Contignasterol, a Highly Oxygenated Steroid with the 'Unnatural' 148 configuration from the Marine Sponge *Petrosia contignata* thiele, 1899", David L. Burgoyne et al., J. Org. Chem. 1992, 57, 525–528.

Bramley et al., "Pharmacological Activity of Pneumocort: A Novel Naturally Occurring Steroid Anti–Asthma Therapy, Isolated From A Marine Sponge," *IBC Conference on Allergic Diseases and Asthma–New Approaches for Treatment,* Washington D.C., 1993.

Bramley et al., "Effect of a Novel Steroid Pneumocort on Ovalbumin Induced Hyperresponsiveness in Guinea Pigs" *American Journal of Respiratory and Critical Care Medicine* 149(4): abstract A768, 1994.

Shoji et al., "Two Unique Pentacyclic Steroids with Cis C/D Ring Junction from *Xestospongia bergquistia* Fromont, Powerful Inhibitors of Histamine Release," *Journal of Organic Chemistry* 57:2996–2997, 1992.

*Primary Examiner*—Kimberly J. Kestler
*Attorney, Agent, or Firm*—Seed and Berry

[57] ABSTRACT

The invention presents compounds useful for the prevention of inflammatory or allergic reaction or the treatment of cardiovascular or haemodynamic disorders having the formula:

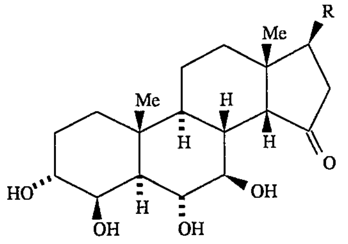

contignasterol nucleus (ring C/D cis)

where R=

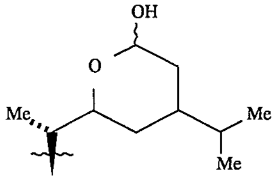

1

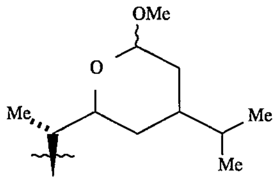

3

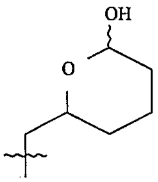

4

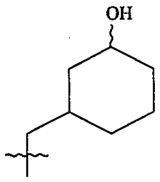

5 or

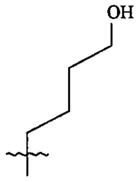

6 or

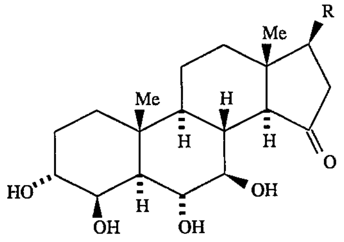

14-epicontignasterol nucleus (ring C/D trans)

where R=

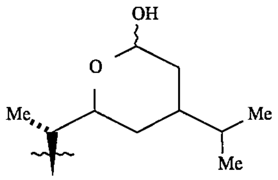

2

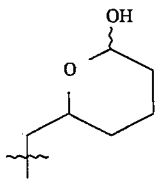

7

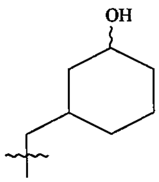

8 or

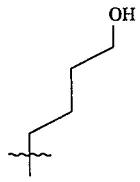

9 or pharmaceutically acceptable acids or salts thereof.

11 Claims, No Drawings

CONTIGNASTEROL, AND RELATED 3-ALPHA HYDROXY-6-ALPHA HYDROXY-7-BETA HYDROXY-15-KETO-14-BETA STEROIDS USEFUL AS ANTI-INFLAMMATORY AND ANTI-THROMBOSIS AGENTS

This application is a continuation-in-part of application Ser. No. 07/996,599, filed Dec. 24, 1992, now abandoned.

FIELD OF THE INVENTION

This invention relates to a new composition of matter, contignasterol, which is useful as an anti-inflammatory agent, an anti-allergen, and as an agent used in the treatment of cardiovascular and haemodynamic disorders, and other diseases.

BACKGROUND OF THE INVENTION

Marine organisms have been the source of many steroids and a number of groups which have chemical and pharmacological activity.

An article in Journal Organic Chemistry, 1992, 57, 2996–2997, entitled "Two Unique Pentacyclic Steroids with Cis C/D Ring Junction from *Xestospongia bergquistia* Fromont, Powerful Inhibitors of Histamine Release", N. Shoji et al., discloses xestobergsterol A (1) (23S-16β, 23-cyclo- 3α,6α,7β,23-tetrahydroxy-5α,14β-cholestan-15 -one) and B (2) (23S-16β,23-cyclo-1β,2β,3α,6α,7β,23 -hexahydroxy-5α,14β-cholestan-15-one), potent inhibitors of histamine release from rat mast cells induced by anti-IgE, are the first report of steroids with both the $C^{16}/C^{23}$ bond and cis C/D ring junction.

SUMMARY OF THE INVENTION

The invention relates to new compositions of matter, and the use of these compositions in the treatment of disease. The basic compound, contignasterol (1), as well as its related compounds, have a new chemical structure as drawn below. It belongs to the steroid class of natural products but it contains a unique set of functional groups attached to the basic cholestane steroid carbon skeleton. The combination of features which make the structure of contignasterol (1) unique are: i) the 3α-hydroxyl, ii) the 4β-hydroxyl, iii) the 6α-hydroxyl, iv) the 7β-hydroxyl, v) the 14β-hydrogen configuration, vi) the 15-ketone functionality, and vii) the cyclic hemiacetal functionality in the steroid side chain which is formed between a hydroxyl functionality at C22 and an ethanal substituent (i.e. a methylene carbon at 28 and an aldehyde carbon at 29) attached at C24. Contignasterol (1) exists as a mixture of R and S stereoisomers at C29. Otherwise the stereochemistry is as drawn in 1.

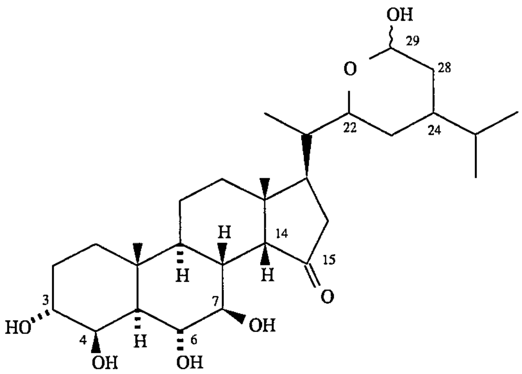
1

In broad terms, the invention pertains to a novel group of contignasterol compounds having the following generic formula:

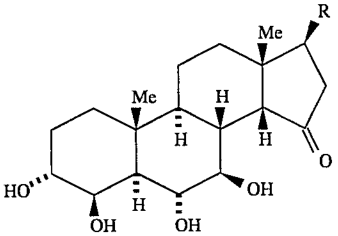

contignasterol nucleus (ring C/D cis)

where R=

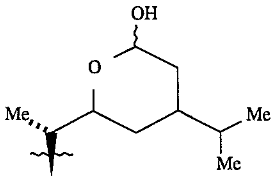
1

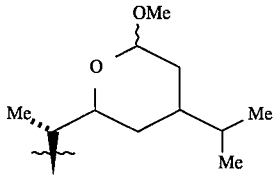
3

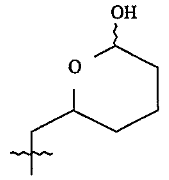
4

-continued

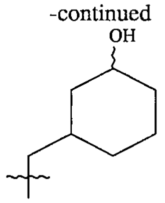

5

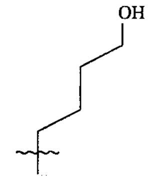

6 and the trans isomer

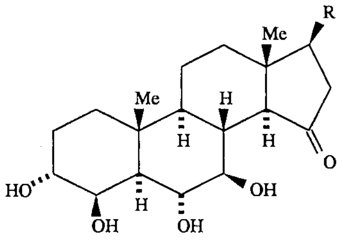

14-epicontignasterol nucleus (ring C/D trans)

where R=

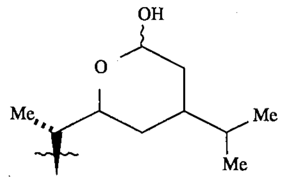

2

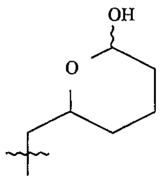

7

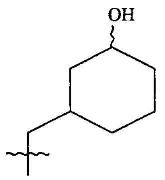

8

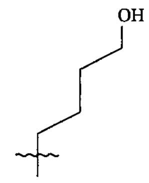

9

The compounds identified above (1 to 9) can be used to prevent inflammatory or allergic reaction when they are administered at a concentration in the range of 0.1 to 100 mg/l, and a pharmaceutically acceptable acid or salts thereof; and a pharmaceutically acceptable carrier.

The compounds identified above (1 to 9) can be used in the treatment of cardiovascular and haemodynamic disorders, when they are administered at 0.1 to 100 mg/l in a pharmaceutically acceptable carrier.

The invention also relates to a method of treating inflammation, asthma, allergic rhinitis, rashes, psoriasis, arthritis, thrombosis and hypotension or hypertension where platelets are involved in a mammal comprising treating the mammal with a therapeutic amount of any one or more of the compounds described above (1 to 9).

DETAILED DESCRIPTION OF THE INVENTION

A first batch of contignasterol (1) was isolated from extracts of specimens of the marine sponge *Petrosia contignata* which were collected by R. Andersen and T. Allen at Madang, Papua New Guinea. Specific locations from which these organisms have been obtained are as follows at a depth of 90 to 120 feet (27 to 37 meters): (1) Dam Awan (Rasch Passage), 145°50' E by 5°09' S, on the outer (east) side of both sides of the passage; (2) On the eastern tip of Pig Is., 145°51' E by 5°10'30" S; and (3) On the barrier reef opposite Wongat Is., 145°49'40" E by 5°08'15" S. The details of the purification and structure elucidation of contignasterol (1) have been published in an article entitled "Conginasterol, Highly Oxygenated Steroid with the 'Natural' 14β Configuration from the Marine Sponge *Petrosia Contignata* Thiele", 1899, in the Journal of Organic Chemistry, Vol. 57, pgs. 525–528, which appeared on Jan. 17, 1992, the subject matter of which is incorporated herein by reference.

The sponge *Petrosia contignata* Thiele was identified by Dr. R. van Soest. A voucher specimen is deposited at the Zoological Museum of Amsterdam. The inventors initiated studies of *Petrosia contignata* because its extracts were active in a L1210 in vitro cytotoxicity assay ($ED_{50}$≈5 μg/mL). A family of previously described poly-brominated diphenyl ethers was found to be responsible for the biological activity. Extracts of the sponge *Petrosia contignata* Thiele contain the highly oxygenated steroid contignasterol (1). Contignasterol is apparently the first steroid from a natural source known to have the "unnatural" 14β proton configuration, 15-Dehydro-14β-ansomagenin, a steroidal aglycon isolated from the saponins of the plant *Solanum vespetilio* also has the 14β proton configuration. However, there was doubt whether the 14β configuration exists in the natural product or was formed by epimerization during the workup. See: Gonzalez, A. G.; Barreira, R. F.; Francisco, C. G.; Rocia, J. A.; Lopez, E. S. *Ann. Quimica* 1974, 70, 250. Aplykurodins A and B, two 20-carbon isoprenoids that are possibly degraded steroids, have relative stereochemistries that would correspond to the 14β proton configuration in a putative steroidal precursor. See Miyamoto, T.; Higuchi, R.; Komori, T.; Fujioka, T.; Mihashi, K. *Tetrahedron Lett.* 1986, 27, 1153. The cyclic hemiacetal functionality in the side chain of contignasterol is also without precedent in previously described steroids.

EXAMPLE 1

Original specimens of *P. contignata* (2.5 kg wet weight) were collected by hand using SCUBA at Madang, Papua New Guinea, and transported to Vancouver frozen over dry ice. The frozen sponge specimens were immersed in methanol (3 L) and soaked at room temperature for 48 hours. Concentration of the decanted methanol in vacuo gave an aqueous suspension (1800 mL) that was sequentially extracted with hexanes (4×500 mL) and chloroform (4×1 L). Evaporation of the combined chloroform extracts in vacuo gave a brown solid (2.1 g) that was subjected to Sephadex LH 20 chromatography (3:1 $MeOH/H_2O$) and reversed-phase HPLC (3:1 $MeOH/H_2O$) to give contignasterol (1) as colorless crystals (153 mg: mp 239°–41° C.).

Contignasterol (1) gave a parent ion in the EIHRMS at m/z 508.3394 Da corresponding to a molecular formula of $C_{29}H_{48}O_7$ (ΔM-0.6 mmu). The $^{13}C$ NMR spectrum of 1 contained 44 resolved resonances (see Experimental Section) and the $^{1}H$ NMR spectrum contained a number of resonances (i.e., δ5.16) that integrated for less than one proton suggesting that the molecule existed as two slowly interconverting isomeric forms. Two of the resonances in the $^{3}C$ NMR spectrum of 1 had chemical shifts appropriate for acetal carbons (δ95.6 (CH) and 90.4 (CH)). An HMQC experiment showed correlations from each of these two carbon resonances to resonances in the $^{1}H$ NMR spectrum of 1 that each integrated for less than one proton. These data were consistent with the presence of a hemiacetal functionality in contignasterol that was undergoing slow spontaneous epimerization.

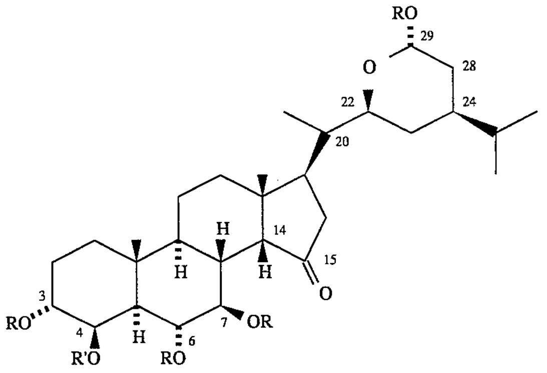

1 R = R' = H
2 R = Ac R' = H
3 R = R' = Ac

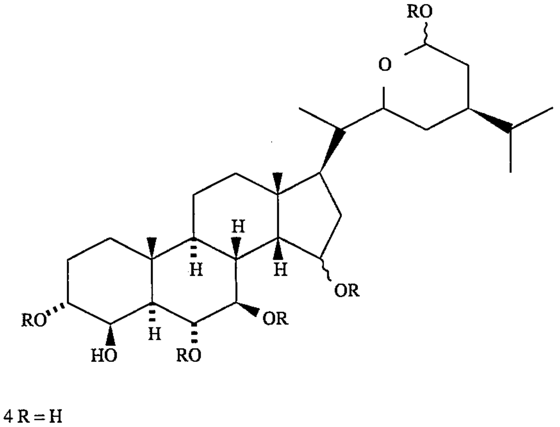

4 R = H
5 R = Ac

Acetylation of contignasterol with acetic anhydride in pyridine gave a mixture of polyacetates that were separated on HPLC to give the tetraacetate 2 as the major product and the pentaacetate 3 as one of the minor products. Evidence for the formation of the tetraacetate 2 came from its $^{13}C$ (δ20.4, 20.6, 20.7, 20.8, 169.1, 169.3, 169.4, 172.7) and $^{1}H$ NMR spectra (δ1.61(s), 1.71(s), 1.82(s), and 1.88(s)) which contained resonances that could be readily assigned to the four acetyl residues (Table I). A peak at mz 616.3605 DA ($C_{35}H_{52}O_9$ ΔM-0.6 mmu) that could be assigned to a $[M^+(C_{37}H_{56}O_{11})$-HOAc] fragment was the highest mass observed in the EIHRMS of the tetraacetate 2. The observation of only the expected 37 resolved resonances in the $^{3}C$ NMR spectrum of 2 (Table I) indicated that the acetylation reaction had successfully eliminated the effects of the hemiacetal epimerization that had complicated the NMR data collected on 1. Consequently, the structure of contignasterol was solved by analysis of the much simpler spectroscopic data collected on the tetraacetate 2.

Experimental Data

Contignasterol (1): obtained as colorless needles from $MeOH/H_2O$ (≈10:1), mp 239°–41° C.; FTIR (film) 1719 $cm^{-1}$; $^{1}H$ NMR (500 MHz, DMSO-$d_6$) δ6.21 (bs), 5.94 (bs), 5.72 (bs), 5.16 (bs), 4.53 (bm), 4.50 (bm), 4.34 (bs), 4.16 (bm), 4.04 (bs), 3.88 (bs), 3.78 (bt, J=10.5 Hz), 3.62 (bs), 3.22 (bt, J=9.4 Hz), 3.05 (bs), 3.00 (bs), 2.38 (bm), 2.09 (bd, J=20.0 Hz), 1.13 (s), 0.93 (s) ppm; $^{13}C$ NMR (125 MHz, DMSO-$d_6$) δ219.4, 219.3, 95.6, 90.4, 75.2, 73.9, 73.8, 70.3, 70.2, 68.6, 68.0, 67.7, 50.7, 50.5, 46.3, 45.8, 45.0, 44.9, 41.3, 41.2, 40.0, 38.8, 38.6, 38.3, 38.2, 36.9, 35.7, 35.5, 34.6, 34.0, 32.5, 32.1, 31.9, 31.8, 23.6, 20.1, 19.6, 19.3, 19.2, 18.9, 18.8, 16.7, 16.7, 14.8 ppm; EIHRMS $M^+$ m/z 508.3394 ($C_{29}H_{48}O_7$ ΔM–0.6 mmu); EILRMS m/z 508, 490, 472, 457, 447, 408, 319, 264, 246, 221, 203, 155, 119, 109.

Contignasterol Tetraacetate (2): Contignasterol (1) (18.0 mg) was stirred in pyridine (2 mL) and acetic anhydride (2 mL) at room temperature for 18 hours. The reagents were removed in vacuo, and the resulting gum was purified using normal-phase HPLC (3:2 ethyl acetate/hexane) to yield the tetraacetate 2 (5.8 mg) and the pentaacetate 3 (≈1 mg). 2: colorless oil; $[\alpha]_D$+63° ($CH_2Cl_2$, c 0.34); FTIR (film) 3477, 1748, 1736 $cm^{-1}$; $^{1}H$ NMR see Table 1; $^{13}C$ NMR see Table I; EIHRMS ($M^+$-HOAc) m/z 616.3605 ($C_{35}H_{52}O_9$ ΔM-0.6 mmu); EILRMS m/z 616, 556, 513, 496, 436, 123, 60, 43.

Contignasterol pentaacetate (3): colorless oil; $^{1}H$ NNR (400 MHz, benzene-$d_6$) δ0.75 (d, J=6.5 Hz, 3H), 0.76 (d, J=6.6 Hz, 3H), 0.77 (d, J=6.8 Hz, 3H), 0.94 (s, 3H), 1.24 (s, 3H), 1.54 (s, 3H), 1.80 (s, 3H), 1.86 (s, 3H), 1.89 (s, 3H), 1.95 (s, 3H), 2.10 (dd, J=3.4, 12.4 Hz), 2.31 (dd, J=10.3, 20.0 Hz), 2.39 (bs), 3.32 (m), 5.10 (m), 5.45 (dd, J=9.0, 12.0 Hz), 5.47 (bs), 5.60 (dd, J=2.2, 9.0 Hz), 6.54 (dd, J=9.1, 10.6 Hz).

Contignasterol Reduction Product 4: $NaBH_4$ (21 mg) was added to a solution of contignasterol (1) (12.5 mg) in isopropyl alcohol (10 mL). The reaction mixture was stirred at room temperature for 1 hour and quenched with $H_2O$ (10 mL). The resulting suspension was extracted with EtOAc (2×10 mL), and the ethyl acetate layer was washed with 1N HCl (10 mL) and $H_2O$ (10 mL). Purification of the ethyl acetate soluble material using reversed-phase HPLC (25:75 $H_2O$/MeOH) gave the reduction product 4 (7.6 mg, 61%): white solid.

Reduction Product Pentaacetate 5: Reduction product 4 (7.6 mg) was stirred in pyridine (1 mL) and acetic anhydride (1 mL) at room temperature for 17 hours. The reagents were removed in vacuo, and the resulting gum was purified on normal-phase HPLC (1:1 ETOAc/Hex) to give the pentaacetate 5: colorless oil; $^{1}H$ NMR (400 MHz benzene-d $_6$) δ0.74 (d, J=6.8 Hz, H27), 0.76 (d, J=6.8 Hz, H26), 0.87 (m H23), 1.03 (d, J=6.8 Hz, H21), 1.04 (s, H19), 1.07 (s, H18), 1.21 (m, H28), 1.25 (m, H1), 1.25 (m, H25), 1.26 (m, H16), 1.48

(m, H23'), 1.59 (s, OAc), 1.60 (m, H2'), 1.62 (m, H28'), 1.63 (m, H5), 1.72 (s, OAC), 1.76 (s, OAc), 1.80 (m, H17), 1.82 (s, OAc), 1.91 (m, $H_2O$), 1.99 (m, H8), 2.00 (m, H2), 2.08 (s, OAc), 2.15 (dd, J=3.6, 7.8 Hz, H14), 3.54 (dd, J=5.9, 9.4 Hz, H22), 3.82 (bm, H4), 5.07 (dd, J=8.9, 11.2 Hz, H7), 5.18 (bm, H3), 5.25 (m, H15), 5.32 (dd, J=8.9, 12.2 Hz, H6), 5.75 (dd, J=2.2, 9.7 Hz, H29) ppm; EIHRMS ($M^{+}$-HOAc) m/z 660.3871 ($C_{37}H_{56}O_{10}$ ΔM−0.2 mmu); EILRMS m/z 660, 642, 615, 600, 540.

The basic cholestane nucleus structures which makes contignasterol different from others are: i) a 3α-hydroxyl, ii) a 6α-hydroxyl, iii) a 7β-hydroxyl, iv) the 14β proton configuration and v) a 15 ketone functionality i.e. 1). The side chain R could be a) linear alkyl groups $CH_3$_$(CH_2)_n$_ where n=0 to 10, (b) the standard cholestane side chain II, or c) oxidized versions of these variations, including in particular the C22 hydroxyl version III and the C23hydroxyl version IV.

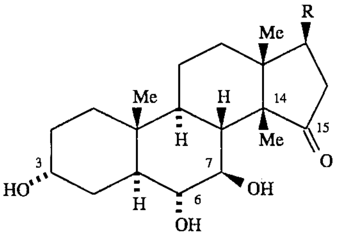

I

R =

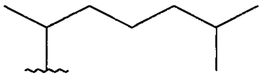

II

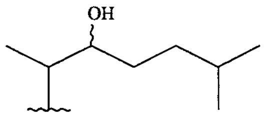

III

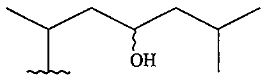

IV

The invention includes the following structures numbered from 1 to 9. Compound 1 consists of the contignasterol (cis) nucleus and the natural side chain R. This compound shows 47% inhibition. Compound 2 consists of the epicontignasterol nucleus (C/D trans) and the natural side chain. This compound has been tested and shows 25% inhibition. Compound 3 has the contignasterol (cis) nucleus with a methyl acetal in the side chain. It shows 12% inhibition. The remaining compounds (4 to 9), on the basis of results to date, should be active and are easy to synthesize.

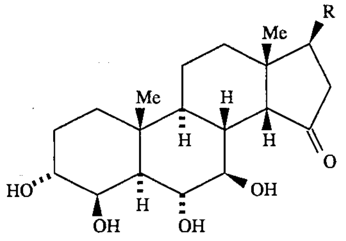

contignasterol nucleus (ring C/D cis)

where R=

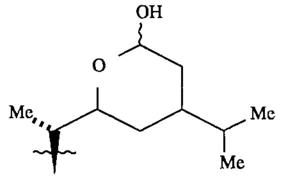

1

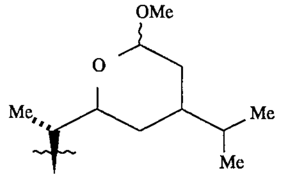

3

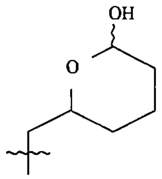

4

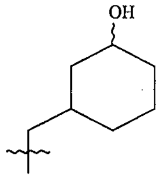

5

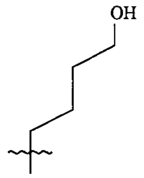

6

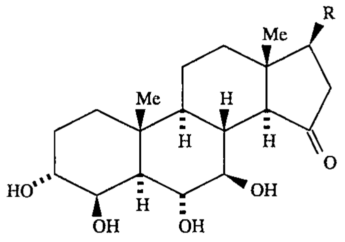

14-epicontignasterol nucleus (ring C/D trans)

where R=

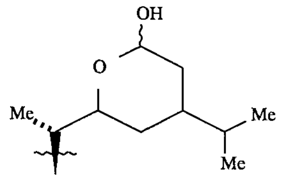

2

-continued

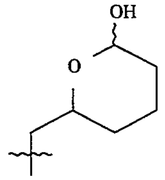

7

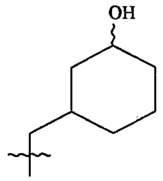

8

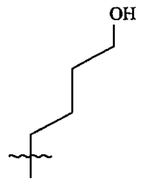

9

The biological data in Table 4 below demonstrates that conversion of the hemiacetal functionality in contignasterol (1) to a methyl acetal (3) leads to a significant decrease in the potency (47% inhibition at 10 μM for 1 to 12% inhibition at 10 μM for 3). This indicates that either a hemiacetal functional group or a hydroxyl group must be present at C29 for full biological potency. It is reasonable to assume that the isopropyl group attached to C24 and the C21 methyl group in the side chain of contignasterol and 14-epicontignasterol are not required for biological activity. Side chains that are lacking the C24 isopropyl and C21 methyl groups have two less chiral centers and therefore they are much simpler to synthesize. The side chain in Compounds 4 and 7 retains the hemiacetal functional group but simply eliminates the C24 isopropyl substituent and the C21 methyl group. The side chain in Compounds 5 and 8 simply replaces the hemiacetal functional group in Compounds 4 and 7 with an alcohol functional group. The side chain in Compounds 6 and 9 places an alcohol functionality on an acyclic appendage the same number of bonds removed from the nucleus as the hydroxyl functional group in the natural side chain found in contignasterol (1) and 14-epicontignasterol (2).

Biological Activity

Anti-Allergic Activity

A major test to confirm the anti-allergic property of contignasterols is the histamine release from human basophils. It has been discovered that contignasterol as defined in the first paragraph of the Summary inhibits histamine release from human basophils present in the blood. We used 1×10 human blood leukocytes from allergic (allergy to grass pollen) individuals and prepared leukocytes. The leukocytes were then challenged with anti-human IgE for the release of histamine. The leukocytes were either exposed to 50 μg/ml of contignasterol or saline alone (control). The amount of histamine released from the leukocytes was measured using radioenzymatic assay. As shown in Table 1, contignasterol inhibited the release of histame by 30–40%. These results suggested that contignasterol is useful as an anti-allergic drug.

TABLE 1

| | Histamine Release (% of Total) |
|---|---|
| Control (no drug), challenge with anti-IgE | 36.4 |
| Contignasterol (50 μg/ml), challenge with anti-IgE | 19.0 |
| Basal release | 9.8 |

Anti-Asthma Activity

We have used the contignasterol as defined in paragraph one of the Summary to block bronchoconstriction induced in guinea pigs. Guinea pigs were sensitized to ovalbumine (OA) that can serve as an antigen. The trachea from these animals after exposure to the antigen (OA) contracted in a similar manner as to in vivo situation. Where the tissue was pretreated with contigosterol, the tissue did not significantly contract after being exposed to the antigen. Table 2 shows the protective effect of contignasterol on OA-induced contraction of tracheal tissues.

TABLE 2

| | Contraction (% of Maximal) | | | |
|---|---|---|---|---|
| Ovalbumine | | Contignasterol (μg/ml) treated | | |
| μg/ml) | Control | 1 | 10 | 50 |
| 0.001 | 6.6 | 0.00 | 0.00 | 0.00 |
| 0.01 | 12 | −7.7 | −8.0 | 0.0 |
| 0.1 | 28.6 | −8.5 | −8.0 | 0.0 |
| 1 | 34.0 | 27.5 | 6.0 | 5.5 |
| 10 | 46.0 | 30 | 16.0 | 11.1 |
| 100 | 55.7 | 39 | 16.6 | 16.6 |
| 300 | 56 | 39.7 | 29.6 | 22 |

The data from Table 2 clearly demonstrates that contignasterol inhibited airway smooth muscle contraction induced by the antigen (OA).

Anti-Thrombolytic Activity of Contignasterol

It was discovered that contignasterol inhibited aggregation of platelets caused by platelet activating factor (PAF) and collagen. PAF is a local mediator of thrombosis. Similarly, collagen exposure of vessel walls leads to the formation of thrombolytic clot in the vessels. Therefore, prevention of the formation of blood clots has direct implication in the treatment of thrombosis and associated cardiovascular diseases.

Table 3 shows that contignasterol inhibits platelet aggregation in response to PAF and collagen.

TABLE 3

| Contignasterol Concentration | Aggregation (% of Control) | |
|---|---|---|
| μg/ml | PAF | Collagen |
| 0 | 100 | 100 |
| 5 | 90 | 70 |
| 10 | 56 | 20 |
| 20 | 44 | 0 |
| 30 | 28 | 0 |
| 50 | 0 | 0 |

PAF and collagen were used at their maximal concentrations to which induced 100% aggregation of platelets. Data from Table 3 clearly demonstrates that contignasterols are potential anti-thrombolytic agents that have usefulness in the treatment of cardiovascular diseases that platelets have a major role.

Table 4 illustrates the relative potencies of different isomers of contignasterol against allergeninduced challenge.

TABLE 4

| Isomer of Contignasterol | [CONC] | % Inhibition |
|---|---|---|
| Cis-Contignasterol (Compound 1) | 10 μM | 43 |
| Trans Contignasterol (Compound 2) | 10 μM | 25 |
| Methyl-acetal Contignasterol (Compound 3) | 10 μM | 12 |

EXAMPLE 2

A second collecting trip to Papua, New Guinea was made Jan. 3, 1994 to Jan. 27, 1994. A large collection of *Petrosia contignata*, the sponge that contains contignasterol, was made. The sponge was very abundant at the collecting sites near Madang were it was originally collected (Example 1). The sponge is widespread and has a very distinctive morphological appearance under water. Any well trained collector of marine invertebrate samples would have no trouble identifying it in the water and collecting sizable amounts. Th 1994 second collection, with little effort, netted over 40 kilograms (88 pounds) of the sponge. Much more could have been collected if a larger quantity had been needed. The inventors have extracted a small sample of the recollected sponge and purified the contignasterol in it using the same methods as discussed in this specification above. The contignasterol so obtained was identical to the original sample of pure compound (Example 1) by spectroscopic comparison. A conservative estimate of the total yield of contignasterol available from this 1994 second 40 kilogram (88 pounds) collection of sponge is in the order of 3 grams of pure compound. The amount that was used in the original chemical structure elucidation (see *Journal of Organic Chemistry,* 1992, 57, 525) and biological evaluation was in the order of 100 mg of pure compound. The sponge is widely dispersed throughout the waters around Papua, New Guinea. Thus it is fair to say that the sponge is common and not rare and that any competent research group could readily repeat the exercise and collect large amounts of the sponge from the plentiful supply available.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

We claim:

1. A compound for the prevention of inflammatory or allergic reaction or the treatment of cardiovascular or haemodynamic disorders comprising:

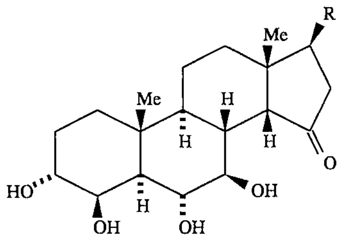

contignasterol nucleus (ring C/D cis)

where R=

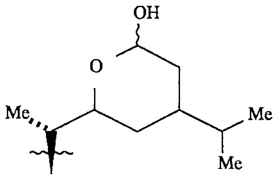

1

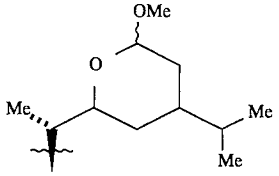

3

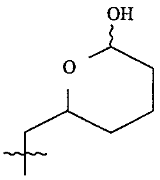

4

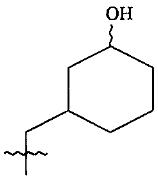

5 or

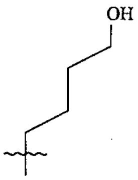

6 or

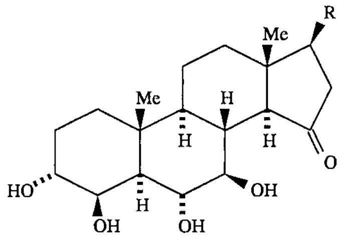

14-epicontignasterol nucleus (ring C/D trans)

where R=

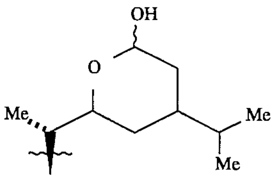

2

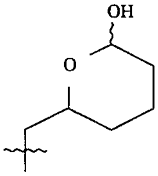

7

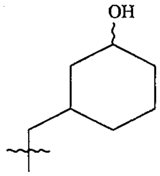

8 or

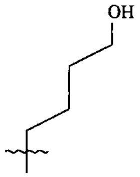

9 or pharmaceutically acceptable acids or salts thereof.

2. A compound for the prevention of inflammatory or allergic reaction or the treatment of cardiovascular or haemodynamic disorders comprising:

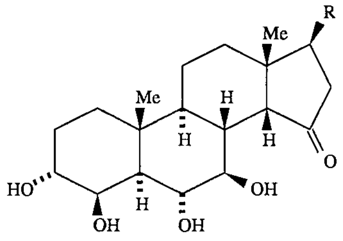

contignasterol nucleus (ring C/D cis)

where R=

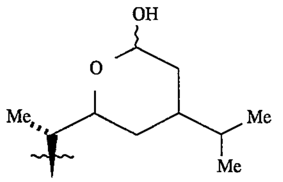

1 or

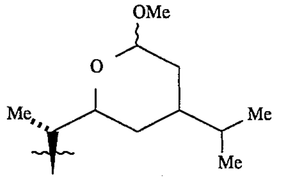

3 or

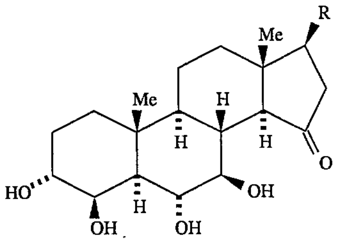

14-epicontignasterol nucleus (ring C/D trans)

where R= .

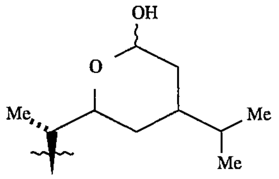

2 or pharmaceutically acceptable acids or salts thereof.

3. A compound according to claim 2 wherein the compound is the contignasterol nucleus (ring C/D cis) where R is formula 1.

4. A compound according to claim 2 wherein the compound is the 14-epicontignasterol nucleus (ring C/D trans) where R is formula 2.

5. A compound according to claim 2 wherein the compound is the contignasterol nucleus (ring C/D cis) where R is formula 3.

6. A composition for the prevention of inflammatory or allergic reaction or the treatment of cardiovascular or haemodynamic disorders comprising a compound of the formula:

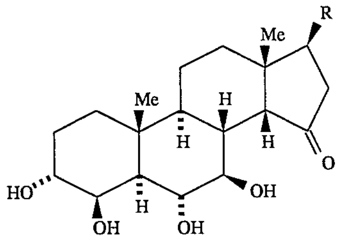

-continued contignasterol nucleus (ring C/D cis)

where R=

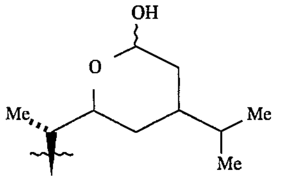

1

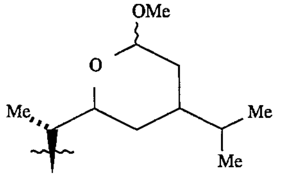

3

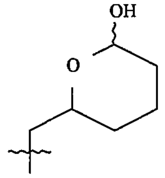

4

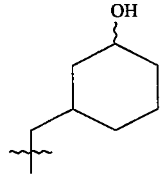

5 or

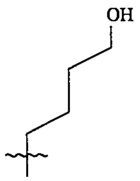

6 or

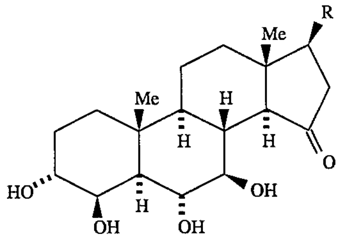

14-epicontignasterol nucleus (ring C/D trans)

where R=

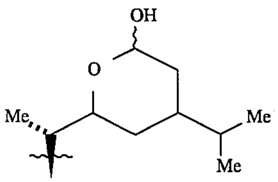

2

-continued

7

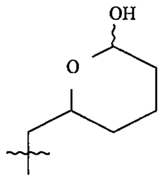

8

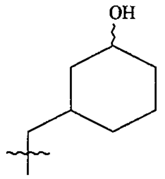

or

9

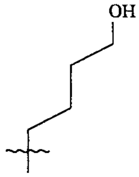

or pharmaceutically acceptable acids or salts thereof, and a pharmaceutically acceptable carrier.

7. A composition for the prevention of inflammatory or allergic reaction or the treatment of cardiovascular or haemodynamic disorders comprising a compound of the formula:

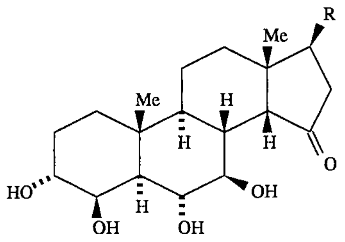

contignasterol nucleus (ring C/D cis)

where R=

1

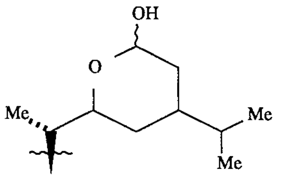

or

3

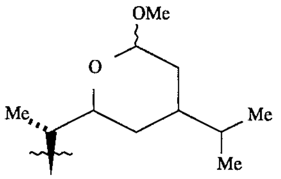

or

-continued

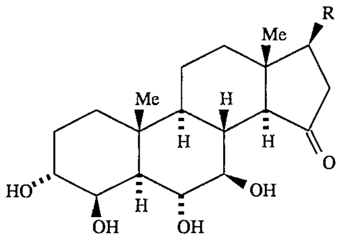

14-epicontignasterol nucleus (ring C/D trans)

where R=

2

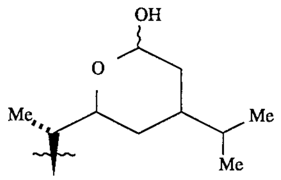

7

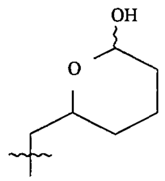

8

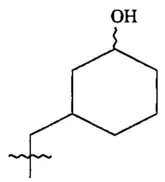

or

9

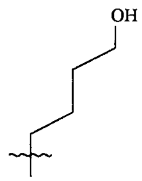

or pharmaceutically acceptable acids or salts thereof, and a pharmaceutically acceptable carrier.

8. A composition according to claim 7 wherein the compound is of the formula:

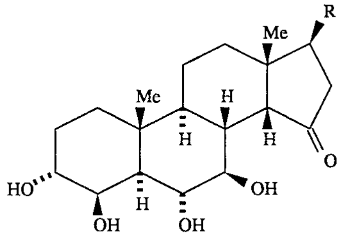

contignasterol nucleus (ring C/D cis)

where R=

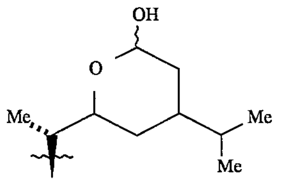

1 or

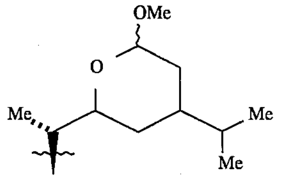

3 or pharmaceutically acceptable acids or salts thereof, and a pharmaceutically acceptable carrier.

9. A composition according to claim 7 wherein the compound is of the formula:

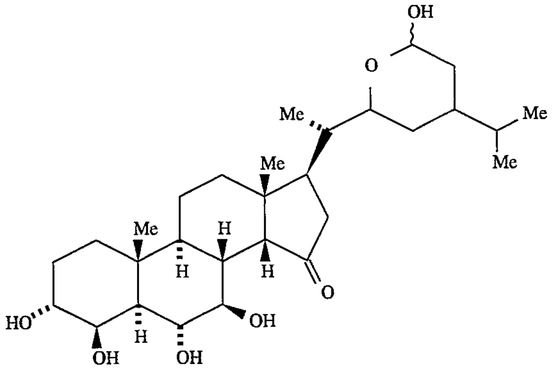

or pharmaceutically acceptable acids or salts thereof, and a pharmaceutically acceptable carrier.

10. A composition according to claim 7 wherein the compound is of the formula:

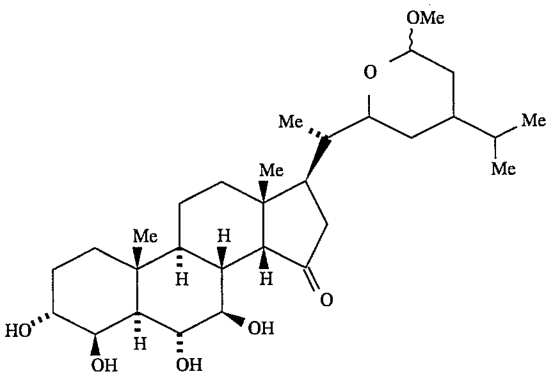

or pharmaceutically acceptable acids or salts thereof, and a pharmaceutically acceptable carrier.

11. A composition according to claim 7 wherein the compound is of the formula:

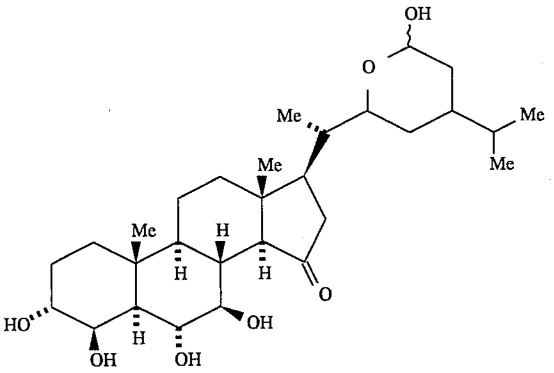

or pharmaceutically acceptable salts thereof, and a pharmaceutically acceptable carrier.

* * * * *